(12) United States Patent
Baravian et al.

(10) Patent No.: US 8,199,323 B2
(45) Date of Patent: Jun. 12, 2012

(54) METHOD OF CHARACTERIZING THE ANISOTROPY OF A SCATTERING MEDIUM AND DEVICE FOR IMPLEMENTING SUCH A METHOD

(75) Inventors: Christophe Baravian, Nancy (FR); François Caton, Chamagne (FR); Jérôme Dillet, Haillainville (FR)

(73) Assignee: Centre National de la Recherche Scientifique—CNRS, Paris (FR)

( * ) Notice: Subject to any disclaimer, the term of this patent is extended or adjusted under 35 U.S.C. 154(b) by 587 days.

(21) Appl. No.: 12/305,604

(22) PCT Filed: Jun. 13, 2007

(86) PCT No.: PCT/FR2007/000983
§ 371 (c)(1),
(2), (4) Date: Jun. 8, 2009

(87) PCT Pub. No.: WO2007/147959
PCT Pub. Date: Dec. 27, 2007

(65) Prior Publication Data
US 2010/0067006 A1    Mar. 18, 2010

(30) Foreign Application Priority Data
Jun. 22, 2006   (FR) .................................... 06 05600

(51) Int. Cl.
*G01J 4/00*   (2006.01)
(52) U.S. Cl. .................. 356/364; 250/559.09; 250/225; 356/338; 356/442; 356/441
(58) Field of Classification Search ............. 250/559.09, 250/225; 356/338, 364, 441, 442
See application file for complete search history.

(56) References Cited

U.S. PATENT DOCUMENTS

| | | | |
|---|---|---|---|
| 6,011,626 A | 1/2000 | Hielscher et al. | |
| 6,022,636 A | 2/2000 | Stocchiero | |
| 2006/0056468 A1 | 3/2006 | Dantus et al. | |
| 2006/0291712 A1* | 12/2006 | Popescu et al. | 382/134 |
| 2007/0171417 A1* | 7/2007 | Cromwell et al. | 356/338 |
| 2008/0170218 A1 | 7/2008 | Dantus et al. | |

OTHER PUBLICATIONS

C. Baravian, F. Caton, J. Dillet, J. Mouget: "Steady light transport under flow: Characterization of evolving dense random media", Physical Review E, vol. 71, No. 066603, Jun. 10, 2005, pp. 1-6, XP002410394, abstract; figure 1, paragraph [0II.].

A. Kienle, L. Lilge, M. S. Patterson, R. Hibst, R. Steiner, B. C. Wilson: "Spatially resolved absolute diffuse reflectance measurements for noninvasive determination of the optical scattering and absorption coefficients of biological tissue", Applied Optics, vol. 35, No. 13, May 1, 1996, pp. 2304-2313, XP002410395, abstract; figure 1, p. 2305, col. 1, lines 27-49, paragraph [003.].

A. H. Hielscher, A. A. Eick, J. R. Mourant, D. Shen, J. P. Freyer, I. J. Bigio: "Diffuse backscattering Mueller matrices of highly scattering media", Optics Express, vol. 1, No. 13, Dec. 22, 1997, pp. 441-453, XP002410396 abstract; figures 1, 2; paragraphs [0001], [0002].

* cited by examiner

*Primary Examiner* — Gregory J Toatley
*Assistant Examiner* — Iyabo S Alli
(74) *Attorney, Agent, or Firm* — Harness, Dickey & Pierce, P.L.C.

(57) ABSTRACT

The invention relates to a method of characterizing a scattering medium. According to the invention, the processing on the electromagnetic radiation scattered by the scattering medium is carried out for an unpolarized signal. In this way, only the anisotrophic incoherent transport of radiation induced by the scattering medium is obtained in the characterization according to the invention. According to the invention, the data representative of the angular variation of the first image representing the unpolarized scattered radiation is representative of the purely isotrophic part of the scattering. Having obtained this purely isotrophic part, it is then possible, according to the invention, to calculate a second image representative of the non-isotrophic part of the scattering. This non-isotrophic part represents the anisotrophic transport of radiation induced by the medium at the moment of scattering.

9 Claims, 10 Drawing Sheets

$$\begin{pmatrix} E_1^s \\ E_2^s \end{pmatrix} = \frac{e^{ikr}}{-ikr} \begin{pmatrix} \tilde{M}_{11} & \tilde{M}_{12} \\ \tilde{M}_{21} & \tilde{M}_{22} \end{pmatrix} \begin{pmatrix} E_1^i \\ E_2^i \end{pmatrix}$$

$$S = \begin{pmatrix} S_0 \\ S_1 \\ S_2 \\ S_3 \end{pmatrix} = \begin{pmatrix} \langle |E_1|^2 + |E_2|^2 \rangle \\ \langle |E_1|^2 - |E_2|^2 \rangle \\ \langle E_1^* E_2 + E_1 E_2^* \rangle \\ i \langle E_1^* E_2 - E_1 E_2^* \rangle \end{pmatrix}$$

$$S^s = \begin{pmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{pmatrix} S^i$$

Figure 2

$$E_1 \rightarrow \begin{pmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{pmatrix} \begin{pmatrix} 1 \\ 1 \\ 0 \\ 0 \end{pmatrix} = \begin{pmatrix} \boxed{m_{11}+m_{12}} \\ m_{21}+m_{22} \\ m_{31}+m_{32} \\ m_{41}+m_{42} \end{pmatrix} I_1$$

$$E_2 \rightarrow \begin{pmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{pmatrix} \begin{pmatrix} 1 \\ -1 \\ 0 \\ 0 \end{pmatrix} = \begin{pmatrix} \boxed{m_{11}-m_{12}} \\ m_{21}-m_{22} \\ m_{31}-m_{32} \\ m_{41}-m_{42} \end{pmatrix} I_2$$

Figure 3

METHOD OF CHARACTERIZING THE ANISOTROPY OF A SCATTERING MEDIUM AND DEVICE FOR IMPLEMENTING SUCH A METHOD

CROSS-REFERENCE TO RELATED APPLICATIONS

This application is a National Phase Entry of International Application No. PCT/FR2007/000983, filed Jun. 13, 2007, claiming priority to FR 06/05600, filed Jun. 22, 2006, both of which are incorporated by reference herein.

BACKGROUND AND SUMMARY

The present invention relates to the field of characterising scattering media.

One important property of scattering media is their anisotropy. Indeed, when particles are deformable and/or anisotropic, there are two possible scenarios. In the first scenario, the particles are oriented and distributed randomly, and the medium comprising these particles remains isotropic on a scale greater than the dimensions of the particles. In this case, the propagation of light through the medium will be substantially identical to that of the randomly distributed isotropic particles. In the second scenario, the particles are oriented in a privileged direction of space. The oriented particles negatively affect the propagation of light in the direction of their orientation and promote it in all other directions. Thus, anisotropy of light propagation can be observed on a large scale, for example when the scattering medium is subject to a sheared or elongating flow.

Methods of characterising a scattering medium are known in the prior art, comprising steps of:
  generating at least one incident electromagnetic beam;
  focussing said incident electromagnetic beam onto a surface of said scattering medium;
  collecting at least one scattered electromagnetic beam corresponding to said at least one electromagnetic beam scattered by said scattering medium;
  generating a first image representative of said at least one scattered electromagnetic beam;
  processing said image;
  characterising said scattering medium based on said process.

Such a method and a device for implementing this method are, for example, known from U.S. Pat. No. 6,011,626. In this document, a characterisation of an isotropic scattering medium is provided by analysing an image representative of a beam scattered by the scattering medium for several polarisation statuses of an incident beam on the scattering medium to be analysed. The device and the method of this document, however, have the disadvantage of not allowing quick access to the anisotropic incoherent transport induced by the scattering medium, and therefore only apply to static or slowly evolving media.

In fact, since the incident radiation emitted onto the scattering medium is also polarised, the effect of polarising the incident radiation combines with the effect of the anisotropic transport of radiation induced by the anisotropies of the scattering medium and prevents access to the anisotropic transport of radiation induced by the anisotropy of the medium. In particular, the device of the aforementioned document involves calculations on all the coefficients of a Mueller matrix, such as illustrated, for example, in FIG. 15 of the aforementioned document. Thus, the device of this document does not in any case allow access to the anisotropic transport of radiation induced by the anisotropy of a scattering medium.

The present invention aims to solve these disadvantages of the prior art. One aim of the present invention is therefore objectively to measure the anisotropic transport of radiation associated with the anisotropy of a scattering medium. Another aim of the present invention is quantitatively to measure the anisotropic transport of radiation associated with the anisotropy of a scattering medium. Another aim of the present invention is to quantify the degree of anisotropy of a scattering medium.

Another aim of the present invention is to measure the effect of the anisotropic transport of radiation associated with the anisotropy of a scattering medium in situ and in a non-intrusive fashion. Another aim of the invention is to measure the effect of the anisotropic transport of radiation associated with the anisotropy of the scattering medium without requiring the use of a polarisation analyser. Another aim of the invention is to define the anisotropic axes of an anisotropic scattering medium.

At least one of these aims is achieved by the present invention, which relates to a method of characterising a scattering medium comprising the following steps:
  generating at least one incident electromagnetic beam;
  focusing said incident electromagnetic beam onto a surface of said scattering medium;
  collecting at least one scattered electromagnetic beam corresponding to said at least one electromagnetic beam scattered by said scattering medium;
  generating a first image representative of said at least one scattered electromagnetic beam;
  processing said image;
  characterising said scattering medium based on said process, characterised in that
  said first image is representative of an unpolarised signal associated with said at least one scattered electromagnetic beam;
  said processing step comprises sub-steps consisting of:
    determining data representative of an angular variation of said first image;
    generating a second image representative of a non-isotropic part of said first image, said second image being calculated using said first image and said data representative of said angular variation; and
  in that
  said characterisation step comprises sub-steps consisting of:
    characterising the anisotropy of said scattering medium with the help of said second image.

Thus, according to the invention, the processes on the electromagnetic beam scattered by the scattering medium are carried out for an unpolarised signal. In this way, only the anisotropic transport of radiation induced by the scattering medium is obtained in the characterisation according to the invention. According to the invention, the data representative of the angular variation of the first image representing the unpolarised scattered radiation is representative of the purely isotropic part of the scattering. This angular variation depends in particular on the nature of the medium and on its concentration, but not on its anisotropy. Having obtained this purely isotropic part, it is then possible, according to the invention, to calculate a second image representative of the non-isotropic part of the scattering. This non-isotropic part represents the anisotropic transport of radiation induced by the medium at the moment of scattering.

The data representative of the angular variation of the first image is, for example, an angular average of the first image, or an angular standard deviation. It should be noted that, in this way, unlike in the method described in U.S. Pat. No. 6,011, 626, it is not necessary to use a polarisation analyser at the output of the scattering medium, since the processes according to the invention are performed directly on an image representative of the scattered radiation.

In one embodiment which makes it possible to calculate the non-isotropic part of the scattering, said second image is calculated by the difference between said first image and said data. In one embodiment which makes it possible to calculate the isotropic part of the scattering, said processing step comprises steps consisting of:
- determining the baric centre of said first image;
- determining said data representative of an angular variation of said first image based on said baric centre.

In order to obtain a first image representative of an unpolarised signal corresponding to said at least one scattered electromagnetic beam, in the aforementioned method,
said step of generating at least one electromagnetic beam comprises steps consisting of:
- generating a first incident electromagnetic beam having a first polarisation;
- generating a second incident electromagnetic beam having a second polarisation, said second polarisation being opposite to said first polarisation;

said step of collecting at least one electromagnetic beam scattered by said scattering medium comprises steps consisting of:
- collecting a first scattered electromagnetic beam corresponding to said first incident beam scattered by said scattering medium;
- collecting a second scattered electromagnetic beam corresponding to said second incident beam scattered by said scattering medium;

and wherein said first image is representative of an unpolarised signal corresponding to said first scattered electromagnetic beam and to said second scattered electromagnetic beam.

In order to simulate an unpolarised scattering beam using polarised incident radiation, the aforementioned method comprises steps consisting of:
- generating a third image representative of said first scattered electromagnetic beam;
- generating a fourth image representative of said second scattered electromagnetic beam wherein said first image is equal to the half-sum of said third image and said fourth image.

The invention also relates to a device for characterising the anisotropy of a scattering medium comprising:
- at least one source of electromagnetic radiation capable of generating at least one incident electromagnetic beam;
- focussing means capable of transmitting said incident electromagnetic beam onto a surface of said scattering medium;
- collection means capable of collecting at least one scattered electromagnetic beam corresponding to said at least one electromagnetic beam scattered by said scattering medium;
- generation means capable of generating a first image representative of said at least one scattered electromagnetic beam;
- processing means capable of processing said first image;
- characterisation means capable of characterising said scattering medium, wherein said first image is representative of an unpolarised signal associated with said at least one scattered electromagnetic beam;
said processing means comprise processing sub-units capable of:
- determining data representative of an angular variation of said first image;
- generating a second image representative of a non-isotropic part of said first image, said second image being calculated using said first image and said data; and wherein
the characterisation means comprise sub-units capable of:
- characterising the anisotropy of said scattering medium with the help of said second image.

According to one embodiment of the aforementioned device, it comprises
- a source of radiation capable of generating an initial electromagnetic beam;
- a first polariser capable of polarising said electromagnetic beam so as to generate a first incident electromagnetic beam having a first polarisation;
- a second polariser capable of polarising said initial electromagnetic beam so as to generate a second incident electromagnetic beam having a second polarisation, said second polarisation being opposite said first polarisation; wherein, said collection means comprise a collection unit capable of
- collecting a first scattered electromagnetic beam corresponding to said first incident beam scattered by said scattering medium;
- collecting a second scattered electromagnetic beam corresponding to said second incident beam scattered by said scattering medium;

and wherein said first image is representative of an unpolarised signal corresponding to said first scattered electromagnetic beam and to said second scattered electromagnetic beam.

Finally, in order to simulate an unpolarised scattered beam, the aforementioned device comprises an arithmetic unit capable of:
- generating a third image representative of said first scattered electromagnetic beam;
- generating a fourth image representative of said second scattered electromagnetic beam and said first image is equal to the half-sum of said third image and said fourth image.

BRIEF DESCRIPTION OF THE DRAWINGS

Further aims and advantages of the invention will become apparent from the following detailed description, made in reference to the appended figures, wherein:

FIG. 2 depicts an output field calculation according to an input field in a scattering medium using Mueller matrices;

FIG. 3 depicts an output field calculation after passing through a scattering medium for an input field with a first polarisation and a second opposing polarisation;

DETAILED DESCRIPTION

Figure 1:
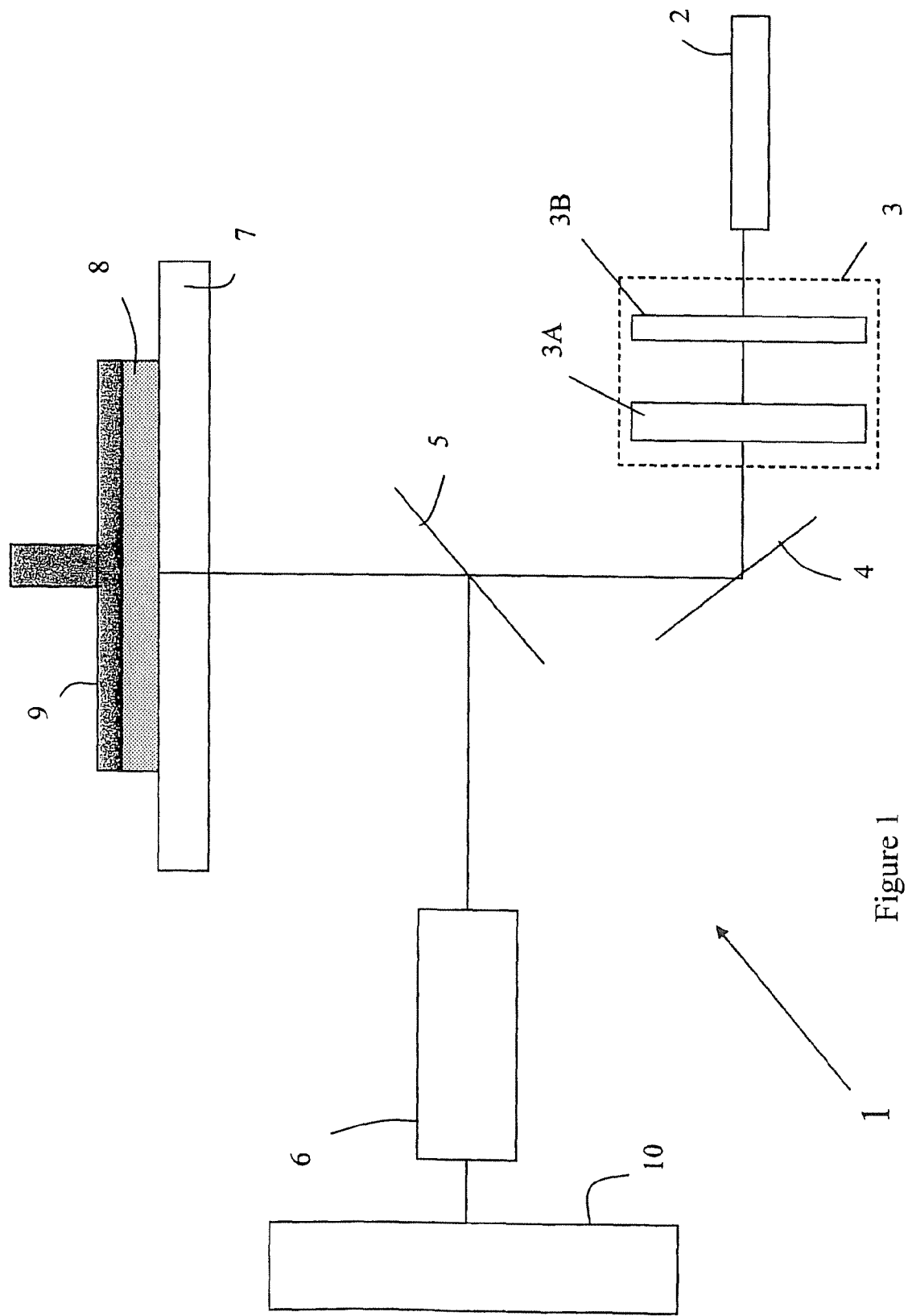
FIG. 1 depicts a device for characterising the anisotropy of a scattering medium according to the invention.

As shown in FIG. 1, a device 1 for characterising the anisotropy of a scattering medium according to the invention comprises a laser diode 2 capable of emitting a monochrome electromagnetic beam at 635 nm, and polarising means 3 comprising a right circular polariser 3A or a left circular polariser 3B. The device 1 also comprises a mirror 4, a beam splitter 5, capable of transmitting the electromagnetic beam towards an assembly comprising a scattering medium 8 to be characterised, positioned between a rheometer 9 and a glass plate 7. The electromagnetic beam is backscattered after passing through the scattering medium 8 towards the splitter 5, which then transmits this backscattered beam towards a CCD camera 6. The CCD camera 6 is connected to processing means 10, for example in the form of a calculator loaded with programs for analysing the properties of the scattering medium 8 by means of one or more analysis images generated by the CCD camera 6. The rheometer 9 is capable of applying a force to the scattering medium 8. This force can be tangential or radial with variable speed.

FIG. 2 shows the relationship between the output field and the input field when crossed by a scattering particle. The matrix of $m_{ij}$ is called Mueller matrix. This matrix is well-known from electromagnetic radiation theory. In FIG. 2, the input/output field with respective parallel and perpendicular components $E^S_1$ and $E^S_2$ is given in relation to the input field with respective parallel and perpendicular components $E^i_1$ and $E^i_2$. It also provides the intensity $S^s$ of the output field according to the intensity $S^i$ of the input field, according to the Mueller matrix $m_{ij}$. A complete description of this theory of electromagnetic interaction and an interpretation of the terms of the Mueller matrix can be found in the publication by C. F. Bohren and D. R. Huffman, "Absorption and scattering of light by small particles", Wiley Science (USA), ISBN: 0-471-29340-7 (1983).

As shown in FIG. 3, according to the invention, the CCD camera 6 of the device 1 described in FIG. 1 is used to capture a first image $I_1$ when the polarisation means are arranged so that the incident light beam $E_1$ on the scattering medium 8 has a first parallel polarisation, and a second image $I_2$ when the polarisation means are arranged so that the incident light beam $E_2$ on the scattering medium 8 has a second perpendicular polarisation. The half-sum of these two images $I_1$ and $I_2$ provides the coefficient $m_{11}$ of the Mueller matrix. The image I obtained using calculation means 10 by the half-sum of the images $I_1$ and $I_2$ corresponds to an unpolarised incident light. In the described example, this unpolarised incident light is obtained using two opposing polarising beams. According to an alternative embodiment not shown, the coefficient $m_{11}$ can also be obtained directly using an unpolarised incident light such as white light.

Figure 4:
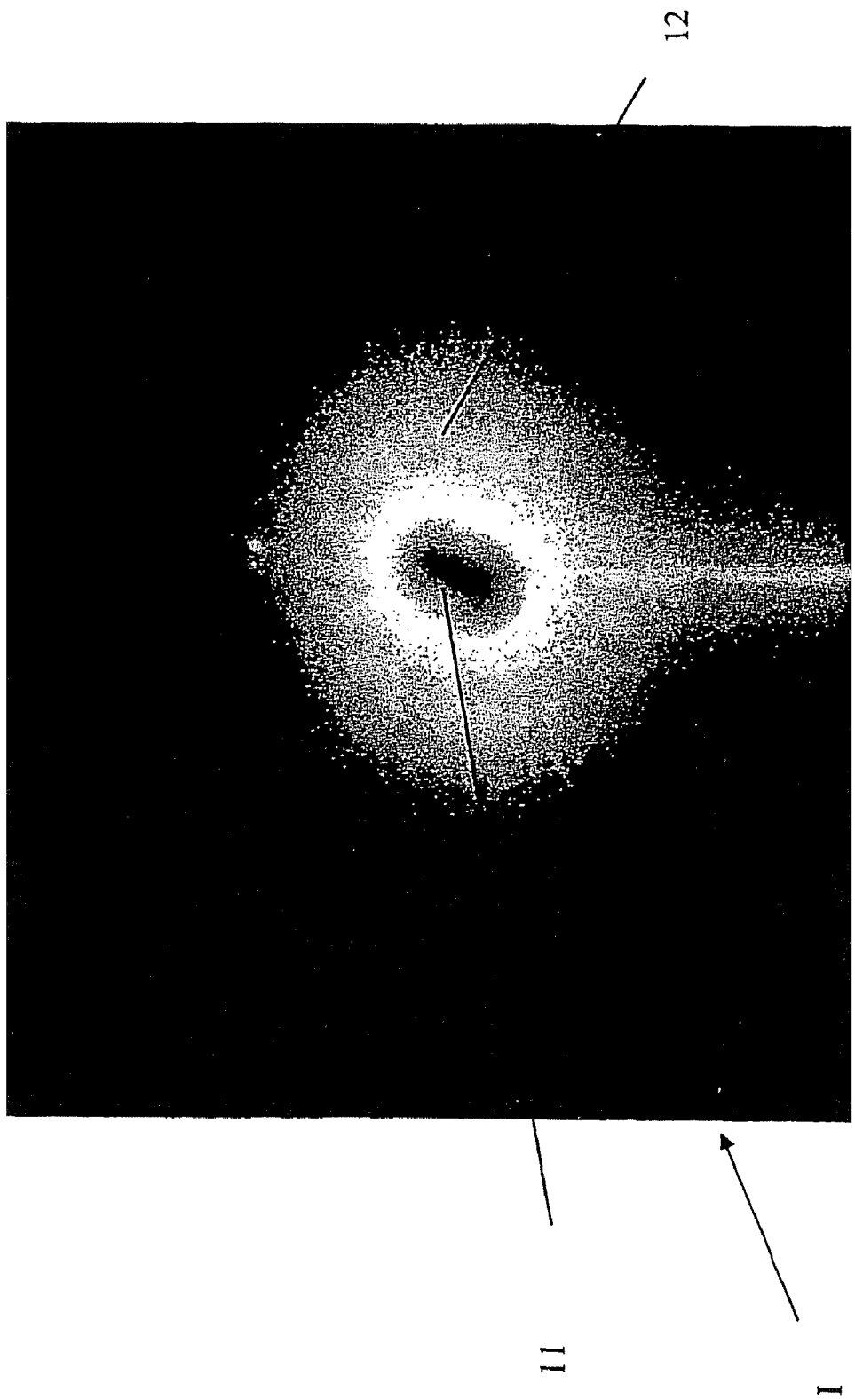
FIG. 4 is an example of an image obtained by a CCD camera according to the invention prior to processing.
Figure 5:
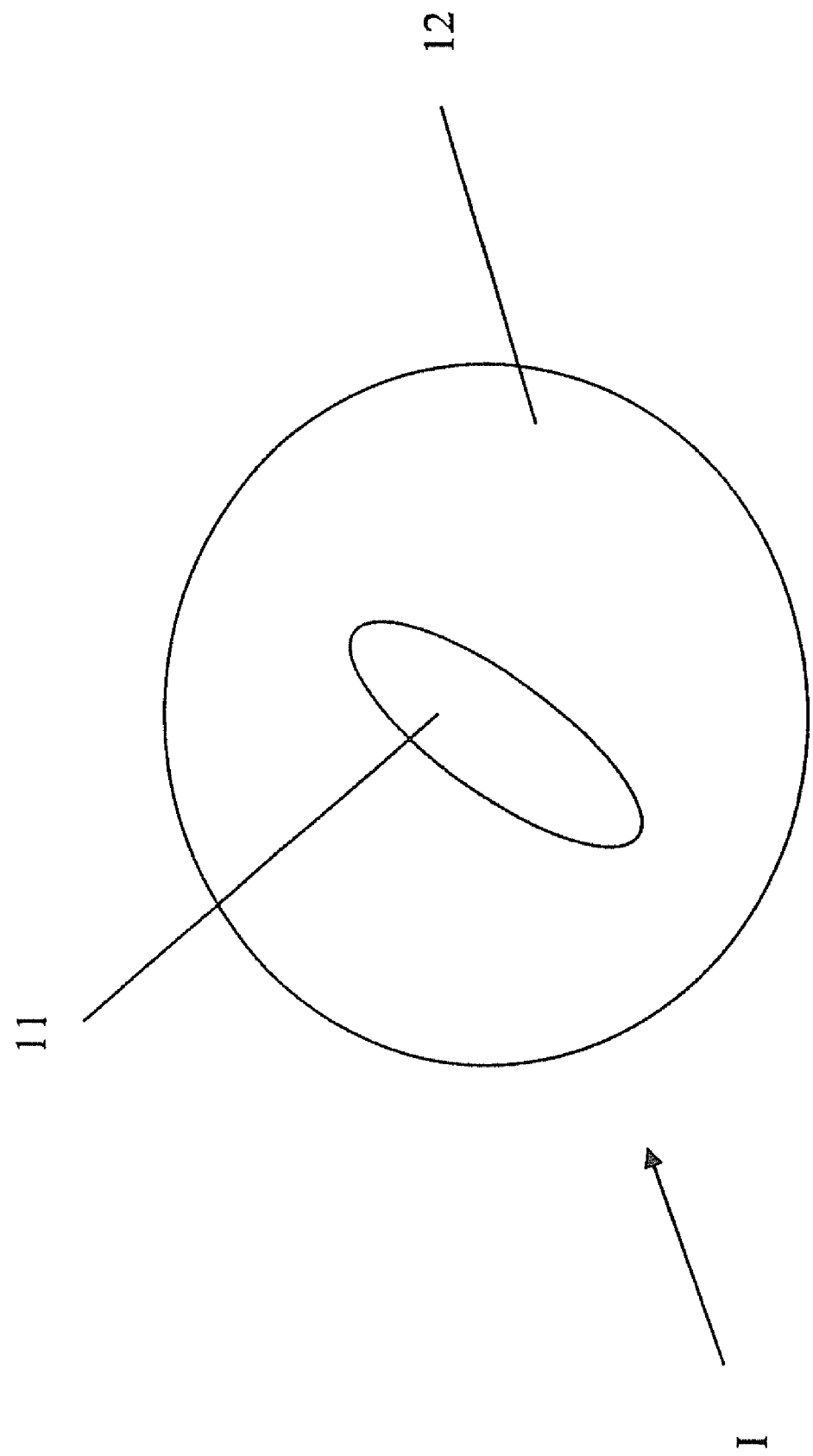
FIG. 5 is a depiction of the characteristic elements of the image in FIG. 4.

The image I obtained is such as depicted in FIG. 4 and FIG. 5. FIG. 4 is an image obtained from a real sample, and FIG. 5 is a depiction of the composition of the real image of FIG. 4.

These two images show angular anisotropy in the form of an oriented central zone 11. This oriented central zone 11 is surrounded by a substantially circular zone 12.

This image makes it possible to obtain a characterisation of the induced anisotropy of the scattering medium under the force of the rheometer 9 of FIG. 1. The Applicant has, in fact, discovered that when the visualised image is angularly isotropic, it means that the objects are either spherical or randomly oriented. When angular anisotropy exists, as is the case in FIGS. 4 and 5, an overall orientation of anisotropic scattering objects or particles takes place. With the help of the image I, the anisotropy is measured by the difference between the image I corresponding to an oriented status and a reference image of an isotropic or random status. This reference status can be calculated by the angular average of the image I based on the baric centre of this image.

Figure 6:
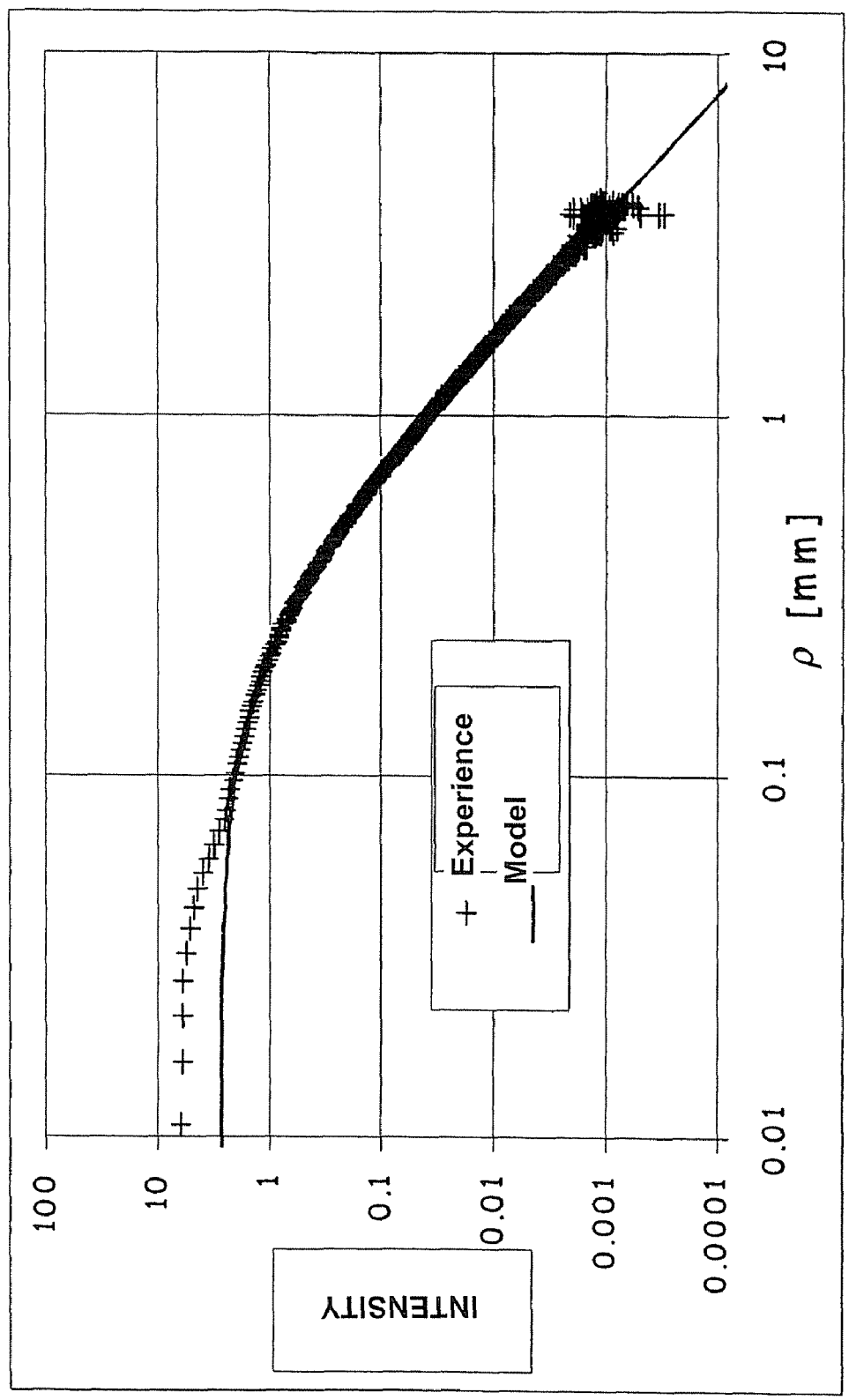
FIG. 6 is a graphic showing the angular average of the intensity of the image according to FIG. 4 according to the radius at the baric centre of the image.

FIG. 6 depicts the intensity of the image I' corresponding to an angular average of the image I, according to the radius starting at the baric centre of the image I. In a well-known manner, the isotropic part of the scattering depends only on the scattering distance I*. This scattering distance I* is the typical distance between two scattering events in a scattering medium. In this figure, the points correspond to a real measurement and the full-line curve corresponds to a modelling of real points, for example such as in the publication by C. Baravian, F. Caton, J. Dillet and J. Mougel, "Steady light transport under flow: characterisation of evolving dense random media", Physical Review E 71, 066603, 2005. This modelling can be used to determine the scattering distance I*.

Figure 7:
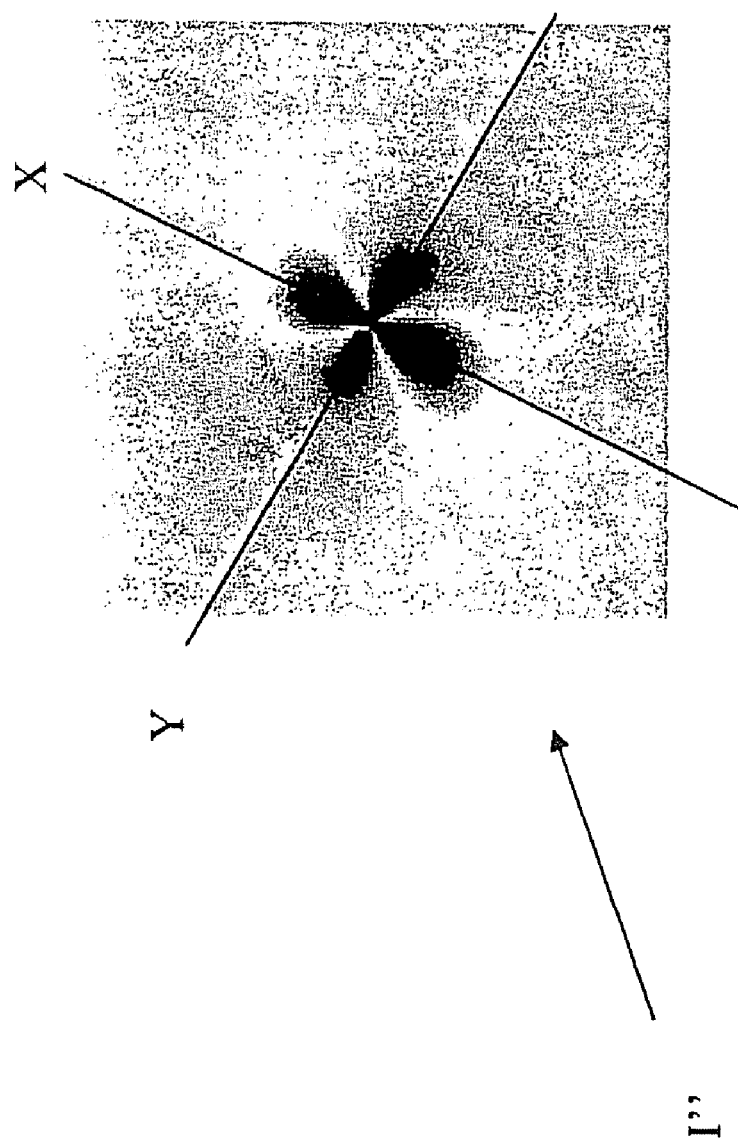
FIG. 7 is an example of an image for characterising anisotropy according to the invention after processing.
Figure 8:
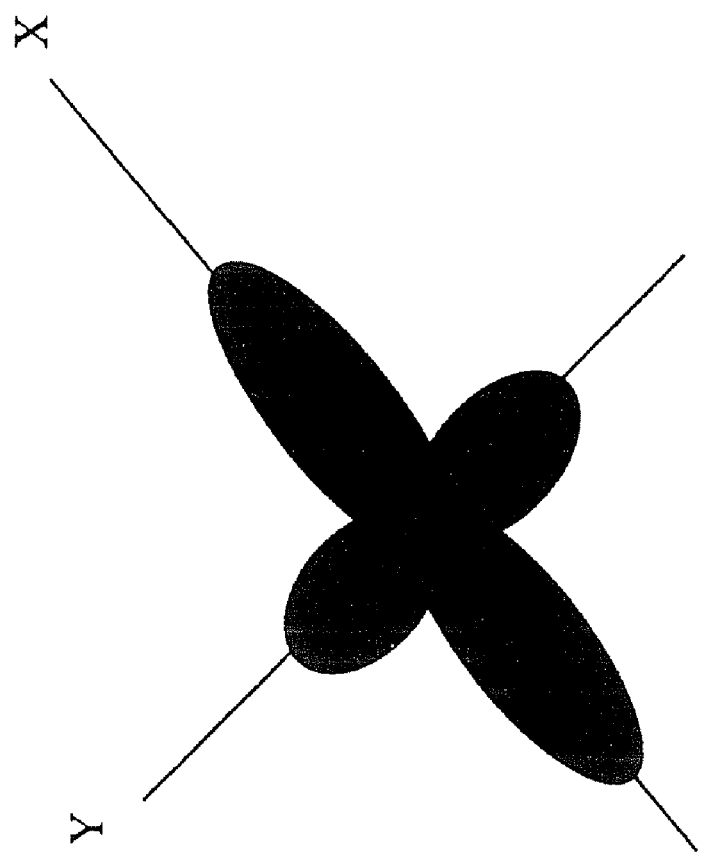
FIG. 8 is a depiction of the characteristic elements of the image of FIG. 7.

FIG. 7 and FIG. 8 show the image I" obtained by subtracting the angular average I' of the image I from this same image I. FIG. 7 is an image obtained for a real sample, and FIG. 8 is a diagrammatic representation of the structure of the image of FIG. 7. The image I" of FIGS. 7 and 8 comprises two series of positive and negative lobes defining privileged axes corresponding to the overall orientation of the anisotropic particles of the scattering medium under the force of the rheometer. This orientation is defined by the axis Y corresponding to the negative lobes.

Figure 9:
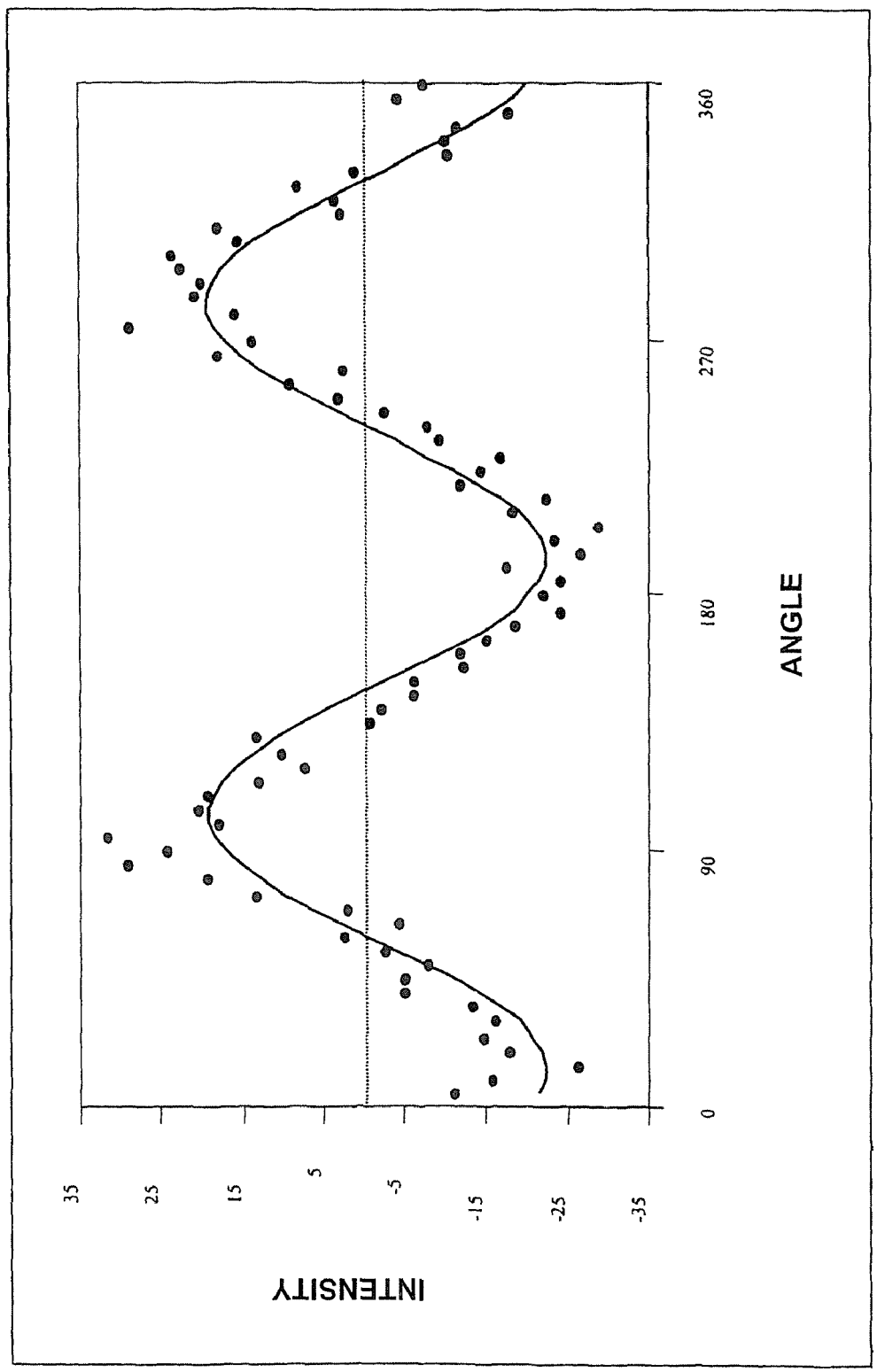
FIG. 9 is a graphic showing the intensity of the anisotropy image according to the invention according to the measurement angle, for a fixed radius at a scattering distance.

FIG. 9 is a graphic showing the intensity of the image I" according to the measurement angle, for a fixed radius at the scattering distance I*. It can be seen that the angular average of the intensity I" is nil by definition.

It is then possible to define the degree of polarisation as the standard deviation of the intensity of the image I", which is to say the standard deviation of the images of FIG. 7 and FIG. 8.

The degree of anisotropy is therefore $$d = \frac{\sqrt{\frac{1}{S}\sum_{x,y}(I''_{x,y})^2 dS}}{\frac{1}{S}\sum_{x,y} I'_{x,y} dS}$$

This degree of anisotropy is a dimensionless value representative of the anisotropic incoherent transport induced by the orientation under the effect of the rheometer. This parameter allows an objective and quantitative measurement of the degree of anisotropy of the scattering medium. It can be seen that this degree of anisotropy is nil for an average isotropic medium.

Figure 10:
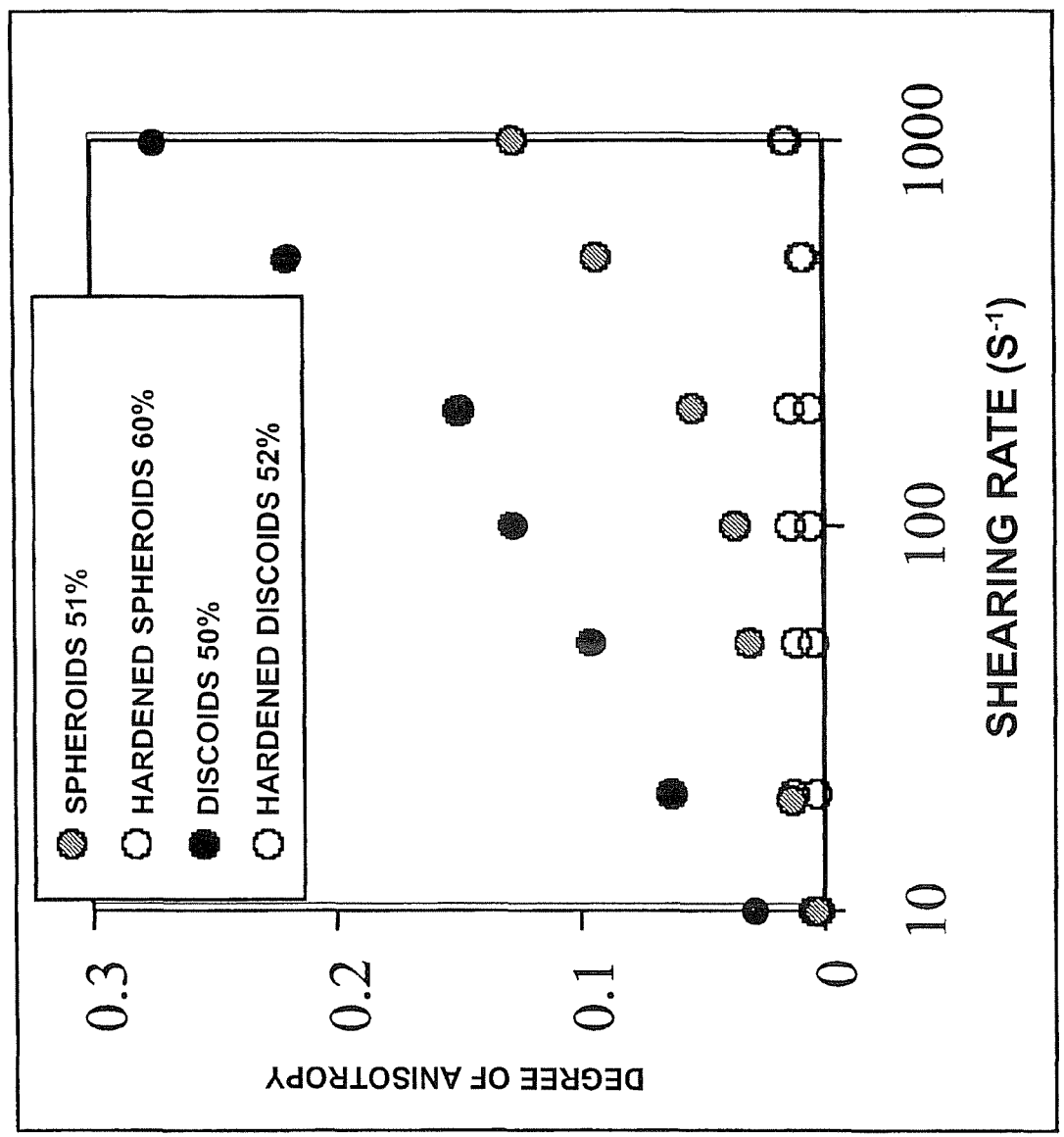
FIG. 10 is a graphic depicting the changes in the degree of polarisation of a scattering medium corresponding to a suspension of red blood cells according to the shearing applied to the scattering medium of red blood cells.

FIG. 10 is a graphic depicting the evolution of the degree of anisotropy of a scattering medium corresponding to a suspension of red blood cells according to the shearing applied to the medium by the rheometer 9. In this figure, it can be seen that the spherical red blood cells, represented by hatched circles and, for example, prepared by osmotic stress, deform less than the disc-shaped red blood cells represented by the full circles. Represented by empty circles, the two types of red blood cells have been hardened and do not show any specific anisotropy.

This type of measurement therefore makes it possible to measure the deformability of the red blood cells and thus to compare different types of blood with one another. This measurement can be used in particular to detect clinical or blood pathologies, since it has proven that a large number of these pathologies are linked to red blood cell deformability, for example in the publication by Langenfeld J E, Machiedo G W, Lyons M, Rush BF Jr, Dikdan G, Lysz T W, "Correlation between red blood cell deformability and changes in hemodynamic function", Surgery 116(5):859-67 (1994). The method such as previously described therefore makes it possible to characterise the anisotropy of an opaque system in visible light. It can be applied to any scattering of anisotropic and/or deformable particles which have collective orientations on a microscopic scale.

An alternative embodiment of the invention is described below. The invention is described above by calculating the angular standard variation of the image I. According to the alternative embodiment, anisotropic transport can be determined by the angular standard deviation calculated at the scattering distance from the baric centre of the image I of FIG. 9. The scattering distance I* can be obtained from the image I as described above in reference to FIG. 6. In more general terms, any analysis of the angular anisotropy of the transport of scattering radiation by the medium obtained by analysing the angular variation of the image I, can be used in the context of the present invention.

The invention claimed is:

1. A method of characterizing a scattering medium comprising the following steps:
   generating at least one incident electromagnetic beam;
   focusing said incident electromagnetic beam on a surface of said scattering medium;
   collecting at least one scattered electromagnetic beam corresponding to said at least one electromagnetic beam scattered by said scattering medium;
   generating a first image representative of said at least one scattered electromagnetic beam;
   processing said image;
   characterizing said scattering medium based on said process, wherein
   said first image is representative of an un-polarized signal associated with said at least one scattered electromagnetic beam exclusive of said incident electromagnetic beam;
   said processing comprises:
      determining data representative of an angular variation of said first image, said angular variation being associated with anisotropy of said scattering medium;
      generating a second image representative of a non-isotropic part of said first image, said second image being calculated using said first image and said data representative of said angular variation; and
   said characterization comprises characterizing the anisotropy of said scattering medium with the help of said second image.

2. The method according to claim 1, wherein said data representative of a variation in an angular variation is an angular average of said image or an angular standard deviation associated with said image.

3. The method according to claim 1, wherein said second image is calculated by the difference between said first image and said data.

4. A method of characterizing a scattering medium comprising:
   generating at least one incident electromagnetic beam;
   focusing said incident electromagnetic beam on a surface of said scattering medium;
   collecting at least one scattered electromagnetic beam corresponding to said at least one electromagnetic beam scattered by said scattering medium;
   generating a first image representative of said at least one scattered electromagnetic beam;
   processing said image;
   characterizing said scattering medium based on said process, wherein said first image is representative of an un-polarized signal associated with said at least one scattered electromagnetic beam;
   said processing comprises:
      determining data representative of an angular variation of said first image;
      generating a second image representative of a non-isotropic part of said first image, said second image being calculated using said first image and said data representative of said angular variation;
      said characterization comprises characterizing the anisotropy of said scattering medium with the help of said second image; and
   wherein said processing step comprises:
      determining the baric center of said first image; and
      determining said data representative of an angular variation of said first image based on said baric center.

5. The method according to claim 1, wherein said step of generating at least one electromagnetic beam comprises:
   generating a first incident electromagnetic beam having a first polarization; and
   generating a second incident electromagnetic beam having a second polarization, said second polarization being opposite to said first polarization;
   said step of collecting at least one electromagnetic beam scattered by said scattering medium comprises steps consisting of:
   said step of collecting at least one electromagnetic beam scattered by said scattering medium comprises steps consisting of:
      collecting a first scattered electromagnetic beam corresponding to said first incident beam scattered by said scattering medium; and
      collecting a second scattered electromagnetic beam corresponding to said second incident beam scattered by said scattering medium;
   wherein said first image is representative of an un-polarized signal corresponding associated with said first scattered electromagnetic beam and with said second scattered electromagnetic beam.

6. The method according to claim 5, wherein said method comprises:
   generating a third image representative of said first scattered electromagnetic beam; and
   generating a fourth image representative of said second scattered electromagnetic beam;
   wherein said first image is equal to the half-sum of said third image and said fourth image.

7. A device for characterizing the anisotropy of a scattering medium, the device comprising:
   at least one source of electromagnetic radiation capable of generating at least one incident electromagnetic beam;
   a focuser capable of transmitting said incident electromagnetic beam onto a surface of said scattering medium;

a collector capable of collecting at least one scattered electromagnetic beam corresponding to said at least one electromagnetic beam scattered by said scattering medium;

a generator capable of generating a first image representative of said at least one scattered electromagnetic beam;

a processer capable of processing said first image; and a characterizer capable of characterizing said scattering medium, wherein said first image is representative of an un-polarized signal associated with said at least one scattered electromagnetic beam exclusive of said incident electromagnetic beam;

said processer comprises processing sub-units capable of:
  determining data representative of an angular variation of said first image, said angular variation being associated with anisotropy of said scattering medium;
  generating a second image representative of a non-isotropic part of said first image, said second image being calculated using said first image and said data; and
wherein the characterizer comprises sub-units capable of characterizing the anisotropy of said scattering medium with the help of said second image.

8. The device according to claim 7, comprising:

a source of radiation capable of generating an initial electromagnetic beam;

a first polarizer capable of polarizing said electromagnetic beam so as to generate a first incident electromagnetic beam having a first polarization; and a second polarizer capable of polarizing said initial electromagnetic beam so as to generate a second incident electromagnetic beam having a second polarization, said second polarization being opposite said first polarization;

wherein,
  said collector comprises a collection unit capable of:
    collecting a first scattered electromagnetic beam corresponding to said first incident beam scattered by said scattering medium; and
    collecting a second scattered electromagnetic beam corresponding to said second incident beam scattered by said scattering medium;
  wherein said first image is representative of an un-polarized signal associated with said first scattered electromagnetic beam and with said second scattered electromagnetic beam.

9. The device according to claim 8, comprising an arithmetic unit capable of:

generating a third image representative of said first scattered electromagnetic beam; and generating a fourth image representative of said second scattered electromagnetic beam, wherein said first image is equal to the half-sum of said third image and said fourth image.

* * * * *